United States Patent
Keinan et al.

(10) Patent No.: US 10,398,447 B2
(45) Date of Patent: Sep. 3, 2019

(54) FIRST-AID TOURNIQUET

(71) Applicant: Waismed Ltd., Herzliya (IL)

(72) Inventors: Emanuel Keinan, Tel Aviv (IL); Moshe Ben Mocha, Tel Aviv (IL)

(73) Assignee: WAISMED LTD., Herzliya (IL)

( * ) Notice: Subject to any disclaimer, the term of this patent is extended or adjusted under 35 U.S.C. 154(b) by 599 days.

(21) Appl. No.: 14/723,811

(22) Filed: May 28, 2015

(65) Prior Publication Data
US 2015/0342615 A1   Dec. 3, 2015

Related U.S. Application Data (60) Provisional application No. 62/118,007, filed on Feb. 19, 2015, provisional application No. 62/006,278, filed on Jun. 2, 2014.

(51) Int. Cl.
*A61B 17/132* (2006.01)
*A61M 25/02* (2006.01)

(52) U.S. Cl.
CPC ......... *A61B 17/1322* (2013.01); *A61M 25/02* (2013.01); *A61M 2025/024* (2013.01); *A61M 2025/0206* (2013.01); *A61M 2025/028* (2013.01)

(58) Field of Classification Search
CPC .... A61M 2025/0206; A61M 2025/024; A61M 2025/028; A61M 25/02; A61M 2025/0039; A61M 2025/0042; A61M 2025/0177; A61M 2025/0183; A61M 2025/0186; A61M 25/0068; A61M 25/104; A61B 17/1322
See application file for complete search history.

(56) References Cited

U.S. PATENT DOCUMENTS

| | | | | |
|---|---|---|---|---|
| 4,470,410 A | * | 9/1984 | Elliott | A61M 5/52 128/877 |
| 5,413,562 A | * | 5/1995 | Swauger | A61M 25/02 128/DIG. 26 |
| 5,897,519 A | * | 4/1999 | Shesol | A61M 25/02 602/75 |
| 5,916,199 A | * | 6/1999 | Miles | A61M 25/02 604/174 |
| 2009/0137962 A1 | * | 5/2009 | Bracken | A61L 24/0031 604/179 |

* cited by examiner

*Primary Examiner* — Brandy S Lee
(74) *Attorney, Agent, or Firm* — Michael J. Feigin, Esq.; Feigin and Fridman (57) ABSTRACT

A tourniquet includes an elongate strip and a tube holding member. The elongate strip includes at least one fastening element attached to the elongate strip. The elongate strip is configured for detachable attachment to the at least one fastening element for providing a tourniquet function and/or a catheter securing function. The tube holding member includes at least one cylindrically shaped wall defining a bore for securing a catheter to a limb.

20 Claims, 7 Drawing Sheets

FIRST-AID TOURNIQUET

RELATED APPLICATIONS

The present application claims priority to U.S. Provisional Patent Application No. 62/006,278 which was filed on Jun. 2, 2014, and U.S. Provisional Patent Application No. 62/118,007 which was filed on Feb. 19, 2015. The contents of the aforementioned applications are incorporated by reference in their entirety.

FIELD OF THE INVENTION

The present disclosure generally relates to the field of first-aid equipment configured to be carried by first-aid providers (medical treatment providers who operate in the field, i.e. outside of medical facilities), in particular tourniquets.

BACKGROUND OF THE INVENTION

First-aid providers can be equipped with, inter alia, first-aid tourniquets (hereinafter the words "first-aid" may be omitted for conciseness only) for treating wounds in the field, until the wounded person be transported to a medical facility for further treatment.

Ideally, first-aid provider equipment is lightweight and/or compact configuring it to be easily portable. Usually, they are single-use items. It will be understood that first-aid tourniquets can differ to hospital tourniquets in that they may be devoid of pneumatic or inflation means, or other electronic devices, or even connectors to such devices etc., since the latter may decrease portability. Such items may also significantly increase purchase cost of such tourniquet, making it unpractical to provide large numbers of personnel with the equipment. Further, first-aid provider equipment is designed to provide a temporary treatment until the wounded reach a medical facility, therefore monitoring equipment is not the aim thereof.

In addition to a tourniquet, first provider equipment or a kit including such equipment may include an intravenous catheter and means for securing such catheter in an operative position on a limb.

An intravenous (IV) catheter can allow administration of fluids and medications, etc. Common practice is to apply tape directly to securely attach the catheter hub and tubing to the patient. Securing the catheter in place to prevent dislodgement thereof from a wounded person is particularly important for field operations in which the wounded person may undergo significant movement during subsequent transportation to a medical facility.

SUMMARY OF THE INVENTION

According to one aspect of the subject matter of the present application, there is provided a first-aid tourniquet configured to function as a tourniquet and as a catheter securing device.

A possible advantage of such dual use device is that it may allow a reduction in first-aid equipment to be carried by a first-aid provider in the field.

Such dual use can be achieved by attaching to a tourniquet a compact and simple catheter securing component. The tourniquet may also comprise a fastening element for use when securing the catheter. Thus with a simple design, i.e. limited components (e.g. one or two components more than is needed for the tourniquet function) a second, catheter securing function can be provided.

According to another aspect of the subject matter of the present application, there is provided a tourniquet comprising: a flexible elongate strip and a tube holding member; the elongate strip comprising: opposite first and second surfaces connected by a peripheral edge; first and second ends; at least one fastening element attached to the elongate strip; and the first and/or second surface being configured for detachable attachment to the at least one fastening element; the tube holding member being attached to the elongate strip and comprising: at least one cylindrically shaped wall defining a bore, and a slit aperture extending along the cylindrically shaped wall.

According to yet another aspect of the subject matter of the present application, there is provided a tourniquet comprising an elongate strip which is stretchable and flexible and comprising a tube holding member attached to the elongate strip.

According to still another aspect of the subject matter of the present application, there is provided a tourniquet comprising: an elongate strip and a tube holding member; the elongate strip being made of stretchable and flexible material and comprising: opposite first and second surfaces connected by a peripheral edge; first and second ends; a first fastening element attached to the elongate strip at the first end; and a second fastening member attached to the elongate strip at the second end; wherein at least one of the first and second surfaces is configured for detachable attachment to the first and second fastening elements; the tube holding member being attached to the elongate strip and comprising: at least one cylindrically shaped wall defining a bore, and a slit aperture extending along the cylindrically shaped wall.

According to yet another aspect of the subject matter of the present application, there is provided a tourniquet comprising a flexible elongate strip and a tube holding member attached to a first surface of the elongate strip, the tube holding member being sized and/or located on the first surface such that at least a portion of one cylindrically shaped wall of the tube holding member is visible when the tourniquet is viewed facing a second surface of the elongate strip which is oppositely located to the first surface of the elongate strip.

According to another aspect of the subject matter of the present application, there is provided a method of applying a tourniquet comprising an elongate strip and tube holding member attached thereto, the comprising: fastening the tourniquet to a limb; then removing the tourniquet from the limb; and then refastening the tourniquet to another portion of the same limb with the tube holding member held against the limb.

To elaborate, the initial step of fastening the tourniquet to the limb is for providing a tourniquet function so that, e.g., a catheter can be used. This step can also comprise an initial sub-step of stretching the elongate strip before fastening it to the limb. The initial stretching movement can assist in compressing the limb when fastened thereto. This step can also comprise fastening a fastening element located at one end of the strip to another portion of the strip. The portion of the strip can be an intermediary portion of the strip located between two ends of the strip.

Subsequent to providing a tourniquet function, a catheter can be applied to the limb.

The step of refastening the tourniquet can further comprise connecting the tube holding member to a catheter applied to the limb. The refastening step can be in order to secure the catheter in place on the limb. More specifically the tube holding member can be connected to a tube or hub of the catheter before the strip is refastened to the limb. Even more specifically the tube holding member can have at least one cylindrically shaped wall for attachment to the tube or hub. The tube holding member can be pressed against the limb with the catheter therebetween. To elaborate, the tube holding member can be flexed by pulling the outer portions (e.g. the planar shaped plates) away from the limb so that the aperture slit(s) open slightly and then the tube holding member can be pressed against the catheter tube portion(s) or hub, which is thereby inserted in the cylindrically shaped wall(s). The catheter tube portion(s) or hub may be able to be held in place due to abutment thereof against the limb. A user can then halt any flexing force on the tube holding member to allow the cylindrically shaped wall(s) close on, and thereby grip, the catheter tube portion(s) or hub. The strip can then be fastened in place on the limb.

The tourniquet and tube holding member can have any of the features mentioned in connection with the other aspects. The step of refastening can include fastening an additional fastening element, i.e. a fastening element other than the fastening element used in the initial fastening step. The additional fastening element can be located at a different end of the strip to the other fastening element. This step can comprise stretching the elongate strip before said refastening. The stretching can assist in ensuring the strip remains in a desired position when refastened to the limb.

In particular, the step of refastening the tourniquet can comprise the elongate strip covering the tube holding member.

Prior to the step of refastening, there can be a step where a catheter tube is looped around the limb such that there are two portions of the tube adjacent to the catheter. Then the step of refastening can comprise a sub-step of placing the tube holding member directly over the two adjacent tube portions and moving the tube holding member against the tube portions and adjacent limb so that the tube portions snap into cylindrically shaped portions thereof.

According to still another aspect of the subject matter of the present application, there is provided a tube holding member comprising: at least one cylindrically shaped wall defining a bore having a longitudinal bore axis, and a slit aperture extending along the cylindrically shaped wall parallel with the bore axis.

According to another aspect of the subject matter of the present application, there is provided a tube holding member comprising: at least one cylindrically shaped wall defining a bore having a longitudinal bore axis, a slit aperture extending along the cylindrically shaped wall, and a groove formed on an opposite side of the cylindrically shaped wall from the slit aperture.

The following features, either alone or in combination, may be applicable to any of the above aspects:

A tourniquet may portable. A tourniquet may be compact. To elaborate, the tourniquet may comprise only an elongate strip and a single rigid component allowing the tourniquet to be folded to a compact shape. All components of a tourniquet may have a planar shape.

A tourniquet may be devoid of pneumatic, hydraulic or electronic components. The tourniquet may be devoid of components configured to connect to pneumatic, hydraulic or electronic components.

An elongate strip may be flexible. An elongate strip may be stretchable. The elongate strip may be made of stretchable and flexible material.

An elongate strip may be configured for detachable attachment to the at least one fastening element. For example, if the at least one fastening element is a hook-and-loop fastener, one or both of the elongate strips first and second surfaces may have an outer layer which detachably bonds (e.g. with loops) to the fastener. Alternatively, the at least one fastener could be a clip or button fastener, etc., and the elongate strip could be configured for attachment thereto with holes or corresponding connection elements etc.

A peripheral edge of the elongate strip may comprise a first minor sub-edge connecting the first and second surfaces at the first end of the elongate strip, a second minor sub-edge connecting the first and second surfaces at the second end of the elongate strip, a first major sub-edge connecting ends of the first and second minor sub-edges and a second major sub-edge opposite the first major sub-edge and connecting the first and second minor sub-edges.

At least one fastening element of the tourniquet may be exactly two fastening elements, namely a first fastening element and a second fastening element.

One of the fastening elements can be for a tourniquet function and another fastening element for a tube securing function. Alternatively, a single fastening element could be used for both functions.

A first fastening element may be attached to a first end of the elongate strip. A second fastening element may be attached to a second end of the elongate strip.

A tube holding member may be attached at the second end of the elongate strip.

Both first and second fastening elements may be attached to a second surface of the elongate strip.

A tube holding member may be attached to a first surface of an elongate strip.

At least one of, or each, of the at least one fastening element, may be a hook-and-loop fastener (e.g., Velcro™).

One of the fastening elements can be located at a diametrically opposite side of the elongate strip from the tube holding member. Without being bound to theory, it is believed that when a fastening element which is configured to be used during a catheter securing function is located at a diametrically opposite side of the elongate strip from the tube holding member it can provide an optimum securing function of the tourniquet on the limb (during the catheter securing function). Stated differently, when the elongate strip is fastened around the limb using the fastening element on the diametrically opposite side of the tube holding member, it is believed such arrangement can directly push the tube holding member against the limb, providing excellent closure of the device and securing of the catheter.

Each fastening element may be configured to fasten when wet.

Each fastening element may be shown to the elongate strip.

A tube holding member may be attached to a first surface of the elongate strip.

A tube holding member may comprise at least a second cylindrically shaped wall element defining a second bore, and a slit aperture extending along the cylindrically shaped wall.

To elaborate, a tube holding member may comprise an additional, i.e. second, cylindrically shaped wall defining an additional bore having longitudinal bore axis, and a slit aperture extending along the cylindrically shaped wall parallel with the bore axis. Both cylindrically shaped walls and the slit apertures thereof may be parallel.

Each slit aperture of the tube holding member may be spaced apart from the elongate strip.

Each slit aperture of the tube holding member may be positioned to be at a diametrically opposite side of the cylindrically shaped wall from the elongate strip.

Slit apertures may both open out from cylindrically shaped walls in the same direction.

A tube holding member may have a planar shape.

A tube holding member height $H_T$ of each cylindrical wall may be greater than a parallel length of the planar shaped plates.

In an axial view of a tube holding member, first and second plates may extend at a height about half-way between the slit aperture and a connection region of the tube holding member and the elongate strip. The first and second plate members may extend at a height closer to the slit aperture or slit apertures than to the connection region.

Each slit aperture of a tube holding member may extend transverse or, preferably, perpendicular to a longitudinal axis of the elongate strip.

Each slit aperture of a tube holding member may have a width less than an inner diameter of a cylindrically shaped wall.

A tube holder member may comprise first and second planar shaped plates extending on opposite sides of the at least one cylindrically shaped wall. The tube holding member may be attached to the elongate strip via the first and second planar shaped plates.

In an axial view of the tube holding member, first and second plates may extend at a height about half-way between the slit aperture and a connection region of the tube holding member and the elongate strip. The first and second plate members may extend at a height closer to the slit aperture or slit apertures than to the connection region.

A peripheral edge of the elongate strip may comprise a first minor sub-edge connecting the first and second surfaces at the first end of the elongate strip, a second minor sub-edge connecting the first and second surfaces at the second end of the elongate strip, a first major sub-edge connecting ends of the first and second minor sub-edges and a second major sub-edge opposite the first major sub-edge and connecting the first and second minor sub-edges.

An axial length of each cylindrical wall may be greater than a distance between the first and second major sub-edges of the elongate strip, when measured perpendicular to a longitudinal axis of the elongate strip.

A tube holding member may be attached to the elongate strip such that the at least one cylindrically shaped wall is partially visible when the tourniquet is viewed facing a side of the elongate strip to which the tube holding member is not attached.

At least one cylindrically shaped wall may protrude further than the elongate strip in a direction transverse to a longitudinal axis of the elongate strip.

A tube holding member may be attached by adhesive to the elongate strip.

An inner surface of each cylindrically shaped wall may be formed with one or more anti-slip ribs oriented transverse or, preferably, perpendicular to a longitudinal bore axis of the cylindrically shaped wall.

Each cylindrically shaped wall may be formed with a groove. The groove can increase the flexibility of the cylindrically shaped wall, allowing the slit aperture to widen as a tube is inserted therethrough into the bore and then close after the tube has passed therethrough. Stated differently, the groove can provide a hinge function. While such groove may weaken the structural strength of the cylindrically shaped wall, it is believed the flexing or hinge-function provided thereby compensates for any disadvantage caused thereby.

A further advantage that may be provided with such construction is that when a tube holding member is pressed against a limb to provide a tourniquet securing function, it can bend slightly to have a curved shape corresponding to a curvature of the limb against which it is pressed.

Each groove may be formed along an outer surface of the cylindrically shaped wall. Each groove may be located at a diametrically opposite portion of the cylindrically shaped wall from the longitudinal slit aperture thereof. Each groove may extend parallel with the longitudinal slit aperture of the cylindrically shaped wall.

The tourniquet may comprise no more than four functional components. The four functional components can be an elongate strip, first and second fastening elements and a tube holding member.

Aspects of the disclosure, in some embodiments thereof, relate to a device for securing an intravenous catheter tube to a patient's body. The device includes an elongate strip configured to surroundingly engage a limb of the patient and a tube holding member configured to engage a catheter tube or hub. The tube holding member may include elements configured to engage the tube at different points along the tube thereby securing the tube as a loop. Furthermore, the tube holding member may be configured to engage the tube from opposite sides thereof. When used to secure the catheter, the elongate strip is wrapped around the limb of a patient, in such manner that part of the elongate strip covers the tube holding member.

The device disclosed herein may obviate the need for applying tape to secure the catheter hub and tube to the patient. Furthermore, the device may be able to enable securing the tube or hub in such manner that the catheter is held sufficiently tight to the patient to avoid relative movement of the catheter when the patient moves or when attended to by medical caregivers.

According to some embodiments, there is provided a device for securing an intravenous catheter to a patient's body. According to some embodiments, the device includes an elongate strip configured to surroundingly engage a limb of the patient and a tube holding member configured to engage a tube or hub of the catheter. According to some embodiments, the tube holding member includes a first and a second bore each bore having a longitudinal axis perpendicular to a longitudinal axis of the elongate strip. According to some embodiments, the first bore comprises a first longitudinal slit aperture extending along the length of the bore. According to some embodiments, the first longitudinal slit aperture may face the patient's limb. According to some embodiments, the second bore comprises a second longitudinal slit aperture extending along the length of the bore. According to some embodiments, the second longitudinal slit aperture may be faced opposite the patient's limb. According to some embodiments, both slit apertures may be configured to face the patient's limb. According to some embodiments, the first and second longitudinal slit apertures may be configured to engage the catheter tube at different points along the length of the tube thereby forming a loop therein.

According to some embodiments, the tube holding member may be attached to the elongate strip at a first end thereof.

According to some embodiments, the first and second bores may have a cylindrically shaped inner wall. The diameter of the cylindrically shaped inner wall may be configured to allow a secure accommodation of the catheter tube, within the first and second bores.

According to some embodiments, the width of the first and second longitudinal slit apertures may be less than the diameter of the catheter tube. According to some embodiments, the width of the first and second longitudinal slit apertures may be configured to allow insertion of the catheter tube into the first and second bores.

According to some embodiments, the first bore may be configured to engage the catheter tube in proximity to a hub of the catheter. According to some embodiments, the second bore may be configured to engage the catheter tube at a point distal to the engagement of the catheter tube in the first bore. According to some embodiments, the loop formed, when the catheter tube is engaged in the first and second bore, is an unkinked loop.

According to some embodiments, the elongate strip may include a fastening assembly configured to fasten opposite ends of the elongate strip; thereby forming a ring structure. According to some embodiments, the tube holding member may include a fastening assembly configured to fasten a second end of the elongate strip; thereby forming a ring structure. According to some embodiments, the fastening assembly may include a first fastening element at a first end of the elongate strip. According to some embodiments, the fastening assembly may include a first fastening element on the tube holding member. According to some embodiments, the second end of said elongate strip may include a plurality of second fastening elements. According to some embodiments, each of the plurality of second fasting elements may be disposed along the length of the elongate strip. According to some embodiments, the first fastening element may be configured to separately (non-concurrently) engage each of the second fastening elements, thereby facilitating formation of ring structures having different diameters. According to some embodiments, the elongate strip may further be for use as an arterial tourniquet.

According to some embodiments, the proximal most fastening element of the plurality of second fastening elements may be disposed at a distance D from a second end of the elongate strip. According to some embodiments, the distance D may at least be of a length corresponding to the length of the tube holding member. According to some embodiments, when the elongate strip surroundingly engages a limb of a patient, the second end of the elongate strip may cover the tube holding member, thereby securing the intravenous catheter to the limb of the patient.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced.

DETAILED DESCRIPTION

As used herein, the term "intravenous catheter" may refer to small, flexible tube placed into a peripheral vein in order to administer medication or fluids, or in order to draw blood. The catheter may be configured to be connected to a limb of the patient, such as but not limited to an arm, a hand, a leg or any other suitable body limb. The catheter is typically introduced into the vein by a needle (similar to blood drawing), which is subsequently removed while the small tube of the cannula remains in place. According to some embodiments, the catheter may include a hub and a tube detachably connected to the hub. According to some embodiments, the hub may include a tip for insertion into the vein, wings for handling the catheter, a valve facilitating injection of drugs, an end for connection of a tube line (typically capped between uses) or any combination thereof.

As referred to herein, the terms "patient" and "subject" may interchangeably be used and may relate to a subject connected to an intravenous catheter.

According to some embodiments, the device includes an elongate strip configured to surroundingly engage the limb of the patient. According to some embodiments, the elongate strip may be made of a stretchable material. According to some embodiments, the elongate strip may be made of a flexible material such as but not limited to a polymeric material (e.g. a polymeric resin). According to some embodiments, the outer surface of the elongating member comprises a water resistant material.

According to some embodiments, the device further includes a tube holding member configured to engage the catheter tube. According to some embodiments, the tube holding member may be attached to the elongate strip at a first end thereof. Alternatively, the tube holding member may be attached to the elongate strip at an attachment point along the length of the elongate strip.

According to some embodiments, the tube holding member includes a first and a second bore each bore having a longitudinal axis perpendicular to the longitudinal axis of the elongate strip. Thus when the elongate strip is wrapped around the limb of a patient, the longitudinal axis of the first and second bore is parallel to the longitudinal axes of the limb.

According to some embodiments, the first bore may include a first longitudinal slit aperture extending along the length of the bore. According to some embodiments, the first longitudinal slit aperture may face the patient's limb. According to some embodiments, the second bore may include a second longitudinal slit aperture extending along the length of the bore. According to some embodiments, the second longitudinal slit aperture may be faced opposite the patient's limb. According to some embodiments, the first and second longitudinal slit apertures may be configured to engage the catheter tube at different points along the length of the tube thereby forming a loop therein. Accordingly, when the catheter securing device is in use, the tube holding member may grasp the catheter tubes from opposite sides thereof. In effect, the configuration of the tube holding member, as disclosed herein, may retain the tube to the tube holding member in situations where the tube is pulled in one direction (e.g. away from the patient) and even in situations where the tube is released from one of the first or second bores of the tube holding member. It is further understood that the (unkinked) loop formed when the catheter tube is engaged in the first and second bores may shorten the length of the tube hanging loose. In addition, the loop formed when the catheter tube is engaged in the first and second bores may reduce the amount of movement of the catheter hub in situations where the catheter tube is manipulated.

It is understood by one of ordinary skill in the art that the tube holding member may include additional bores configured to engage the catheter tube. Non-limiting examples of the number of bores may include 2, 3, 4, 5 bores or more. Each possibility is separate embodiment. According to some embodiments, a tube holding member having more than two bores may be configured to engage the same catheter at additional points along the length thereof thereby facilitating the formation of multiple loops in the catheter tube. Alternatively or additionally, a tube holding member having more than two bores may be configured to engage more than one catheter tube such as but not limited to 2, 3 or more catheter tubes.

According to some embodiments, the first and second bores may have a cylindrically shaped inner wall. The diameter of the cylindrically shaped inner wall may be configured to allow a secure accommodation of the catheter tube, within the first and second bores. As used herein the term "secure accommodation" may refer to the catheter tube being hold within any one of the bores of the tube holding member in such manner that the tube has limited possibility of movement within the bore yet the bore does not press upon the tube. Consequently, no change in the diameter of the tube is incurred when the tube is correctly placed within the bore.

According to some embodiments, the width of the first and second longitudinal slit apertures may be less than the diameter of the catheter tube. According to some embodiments, the width of the first and second longitudinal slit apertures may be configured to allow insertion of the catheter tube into the first and second bores. Accordingly the width of the split is such that the tube may be inserted into the bore without applying excessive force which may harm the patient, yet the tube may have to be "squeezed" during the insertion process. The width may thus serve to ensure that the catheter tube will not easily slip out of the bores, for example when the patient moves.

According to some embodiments, the first bore may be configured to engage the catheter tube in proximity to the hub of the catheter. As used herein the term proximity may refer to less than 0.5 cm less than 1 cm, less than 2 cm, less than 5 cm or less than 10 cm. Each possibility is a separate embodiment.

According to some embodiments, the second bore may be configured to engage the catheter tube at a point distal to the engagement of the catheter tube in the first bore. According to some embodiments, the distance (on the catheter tube) between the engagement point into the first bore and the engagement point into the second bore is such that formation of an unkinked loop is facilitated. As a non-limiting example, when the catheter is fixed to an arm of the patient, the catheter tube may form a loop around a finger of the patient, between the first and second engagement points.

According to some embodiments, the elongate strip may include a fastening assembly configured to fasten opposite ends of the elongate strip; thereby forming a ring structure. According to some embodiments, the tube holding member may include a fastening assembly configured to fasten a second end of the elongate strip; thereby forming a ring structure therewith. It is understood to one of ordinary skill in the art that the fastening assembly may be any suitable fastening assembly, such as, but not limited to, buttons, hooks, hook-and-loop, straps, zippers, clips, Velcro™ fasteners and the like. Each possibility is a separate embodiment. According to some embodiments, the fastening assembly includes at least two fastening elements, such as, but not limited to when using buttons, hooks, Velcro™ fasteners and the like. Alternatively, the fastening element may be a single element, such as, but not limited to, when using certain clips.

According to some embodiments, the fastening assembly may include a first fastening element at a first end of the elongate strip. According to some embodiments, the fastening assembly may include a first fastening element on the tube holding member strip. According to some embodiments, the second end of said elongate strip may include a plurality of second fastening elements. According to some embodiments, each of the plurality of second fasting elements may be disposed along the length of the elongate strip. Accordingly, fastening the first fastening element to any one of the second fastening elements may facilitate formation of a ring structure; the diameter of the ring structure depending on the distance of the second fastening element from the second end of the elongate strip. As used herein, the term "ring structure" may refer to a loop being formed along the length of the elongate strip. It is thus understood to one of ordinary skill in the art that the term includes, but is not limited to, a full ring. For example a ring may be formed involving only half of the elongate strip and such "lasso" structures are encompassed within the term "ring structure". It is further understood that the term "ring structure" includes, but is not limited to, a circular ring structure but may include any round structures formed when two ends of a flexible material are joined.

According to some embodiments, when no catheter tube is connected to the catheter hub, the elongate strip may serve as a hub securing element, having no tubes engaged in the first and second bores.

According to some embodiments the elongate strip may serve as a hub securing element, wherein the hub is held in one of the bores.

According to some embodiments, the elongate strip may further be for use as an arterial tourniquet. For example, the elongate strip may be used as an arterial tourniquet by connecting the first fastening element to one of distal most second fastening elements. Alternatively, the elongate strip may be used as an arterial tourniquet by sliding and fastening a fastening assembly along the length of the elongate strip.

According to some embodiments, the second fastening element, most proximal to the second end of the elongate strip may be located at a distance D from the second end (the end opposite to the tube holding member) of the elongate strip. According to some embodiments, the distance D corresponds to the length of the tube holding member, such that the second end of the elongate strip covers the tube holding member when the elongate strip surroundingly engages a limb of a patient. According to some embodiments, the elongate strip further comprises an attachment element (e.g. a Velcro™ strap) configured to attached the elongate strip at the other side of the covered tube holding member. It is understood that such configuration contributes to securing the intravenous catheter to the limb of the patient.

Figure 1:
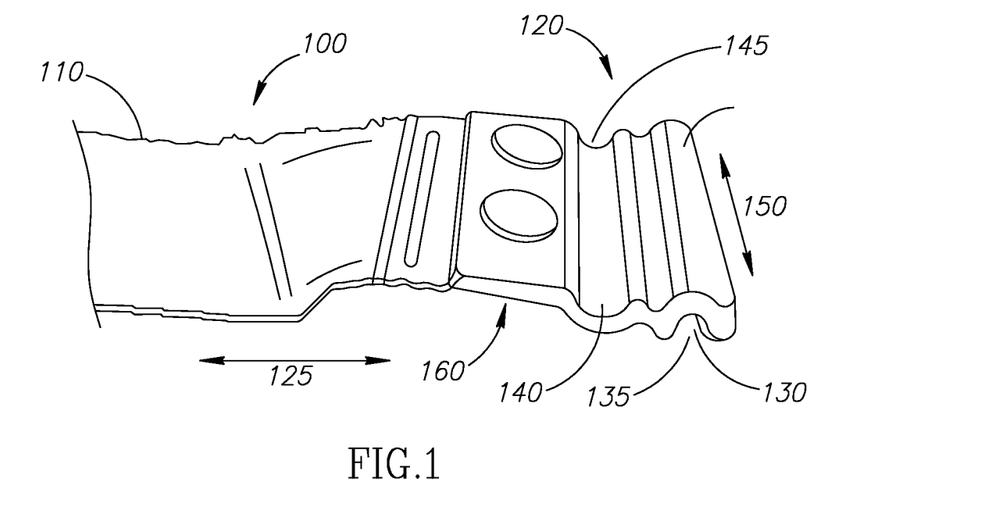
FIG. 1 illustrates a device including an elongate strip and a tube holding member, according to some embodiments.

Reference is now made to FIG. 1, which illustrates a device 100 according to some embodiments. The device 100 includes an elongate strip 110 and a tube holding member 120. Tube holding member 120 includes a first bore 130 and a second bore 140, each bore having a longitudinal axis (arrow 150) perpendicular to the longitudinal axis (parallel to arrow 125) of the elongate strip. First bore 130 includes a first longitudinal slit aperture 135 extending along the length of the bore facing the patient's limb. Similarly, second bore 140 include a second longitudinal slit aperture 145 facing opposite the patient's limb. Second bore 140 is here proximal to elongate strip 110 (as compared to first bore 130). However, it is clear to one of ordinary skill in the art that an opposite configuration (in which first bore 130 is the proximal most to elongate strip 110) is likewise applicable and such fall within the scope of this disclosure. The device 100 further includes a fastening assembly 160. Fastening assembly is here depicted to be part of tube holding member 120. However, as disclosed hereinabove, a fastening assembly may also be part of elongate strip 110.

Reference is now made to FIGS. 2-5, which illustrate a device at different stages of assembly.

Figure 2:
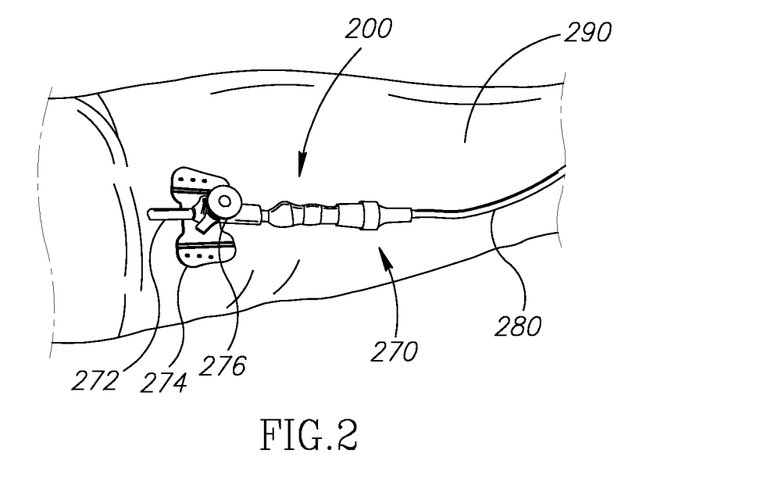
FIG. 2 illustrates a catheter connected to a person's limb.

FIG. 2, depicts an intravenous catheter 200 inserted into an arm 290 of a patient. Intravenous catheter 200 includes a catheter hub 270 and a catheter tube 280. Catheter hub 270 includes a tip 272 for insertion into the vein, wings 274 for handling the catheter, and a valve 276.

Figure 3:
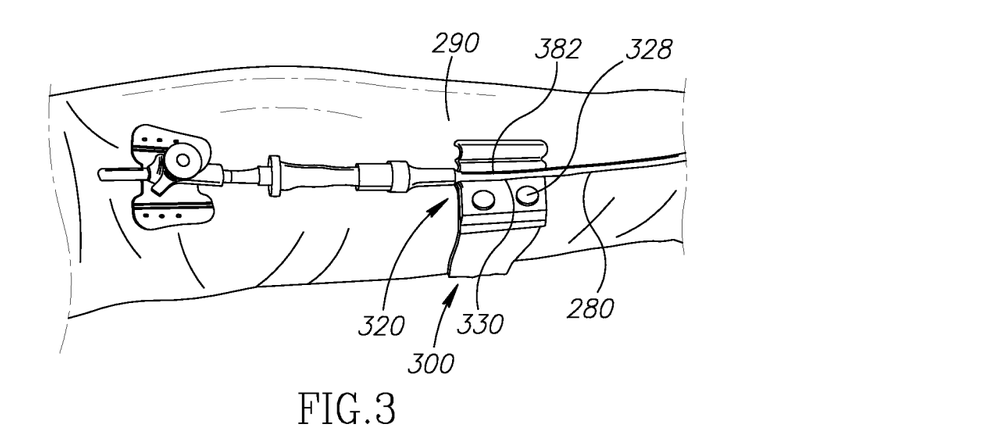
FIG. 3 illustrates a device including an elongate strip and a tube holding member in which a catheter tube is secured in a first bore of the tube holding member, according to some embodiments.

FIG. 3 depicts a stage of applying a device 300 to the arm 290 of the patient. At this stage, part 382 of catheter tube 280 is engaged in a first bore 330 of tube holding member 320.

Figure 4:
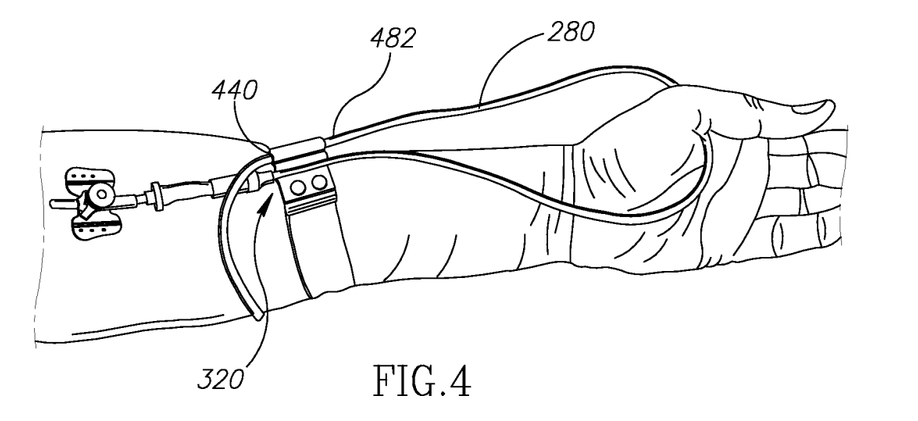
FIG. 4 illustrates a device including an elongate strip and a tube holding member in which a catheter tube is secured in a first and second bore of the tube holding member, according to some embodiments.

At the next stage, depicted in FIG. 4, catheter tube 280 is engaged in second bore 440 of tube holding member 320 by inserting a second part 482 (distal to part 382) of catheter tube 280 into bore 440.

Figure 5:
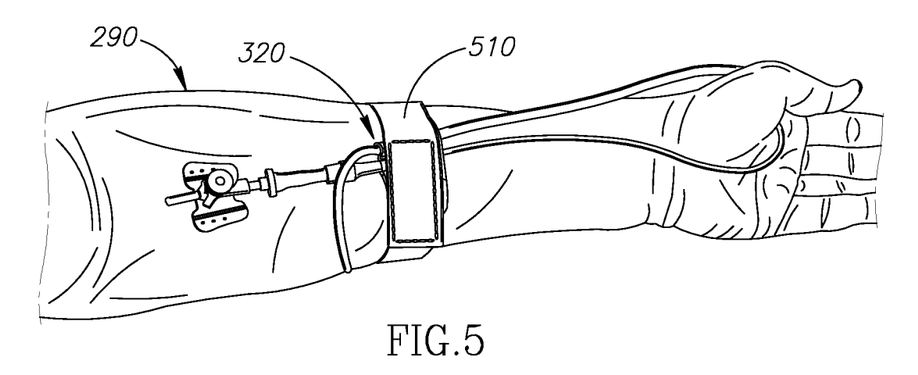
FIG. 5 illustrates a device including an elongate strip and a tube holding member having a catheter tube secured in a first and second bore of the tube holding member, and having the elongate strip wrapped around a limb, according to some embodiments.

Finally, as depicted in FIG. 5, elongate strip 510 is wrapped around arm 290 and fastened through fastening assembly in such manner that elongate strip 510 covers tube holding member 320.

Figure 6A:
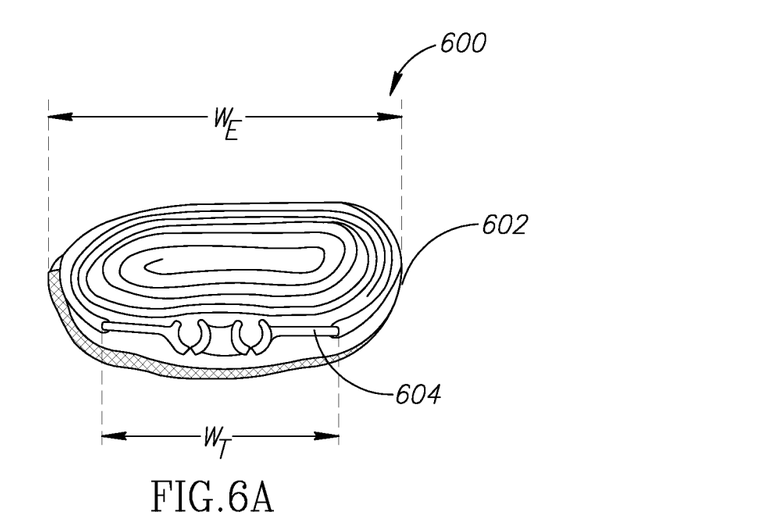
FIG. 6A illustrates a side view of a tourniquet in a folded, portable state.
Figure 6B:
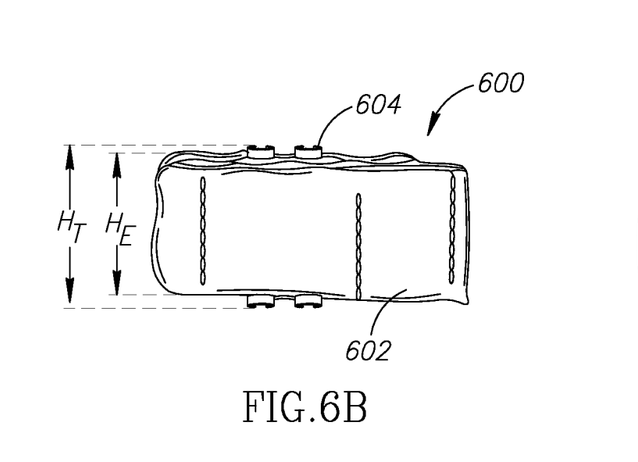
FIG. 6B illustrates a front view of the folded tourniquet in FIG. 6A.
Figure 6C:
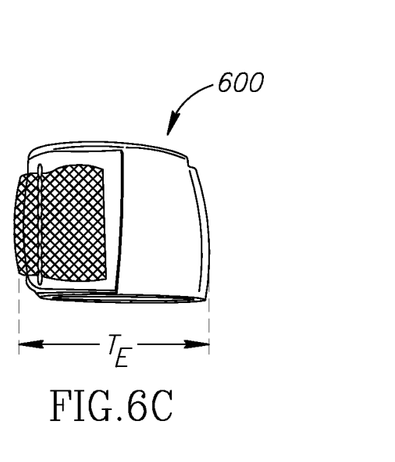
FIG. 6C illustrates another side view of the folded tourniquet in FIGS. 6A and 6B.

Reference is now made to FIGS. 6A to 6C, which illustrate a tourniquet 600 in a folded state.

The tourniquet 600 can comprise an elongate strip 602 and a tube holding member 604 attached thereto.

As shown in FIG. 6A the tube holding member 604 can be considered to have a generally planar shape. A tube holding member width $W_T$ is shown. Notably an elongate strip width $W_E$ in the folded state can be less than twice the tube holding member width $W_T$.

In FIG. 6B, a tube holding member height $H_T$ is shown. Notably an elongate strip height $H_E$ in the folded state is almost the same as the tube holding member height $H_T$. Certainly, the tube holding member height $H_T$ may be less than twice the elongate strip height $H_E$.

In FIG. 6C, it can be appreciated that an elongate strip thickness $T_E$ can be less than the tube holding member width $W_T$ (FIG. 6A) and even can be less than the tube holding member height $H_T$ (FIG. 6B).

Without being bound to the specific ratios mentioned above, it will be understood that the tourniquet 600 can be configured to be folded to a compact and hence portable state.

Figure 6D:
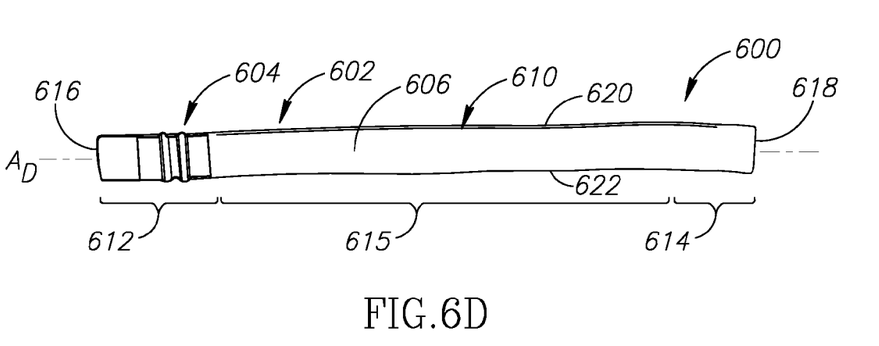
FIG. 6D illustrates a front view of the tourniquet in FIGS. 6A to 6C, in an unfolded state.
Figure 6E:
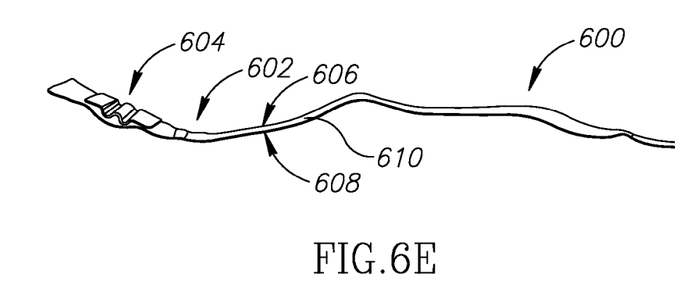
FIG. 6E illustrates a side view corresponding to the side view in FIG. 6A, of the tourniquet in FIGS. 6A to 6D, in an unfolded state.
Figure 6F:
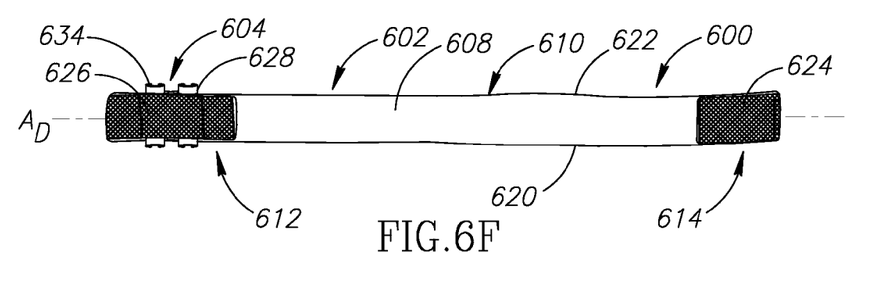
FIG. 6F illustrates a rear view, i.e. a view opposite to the front view shown in FIG. 6A, of the tourniquet in FIGS. 6A to 6E, in an unfolded state.
Figure 7A:
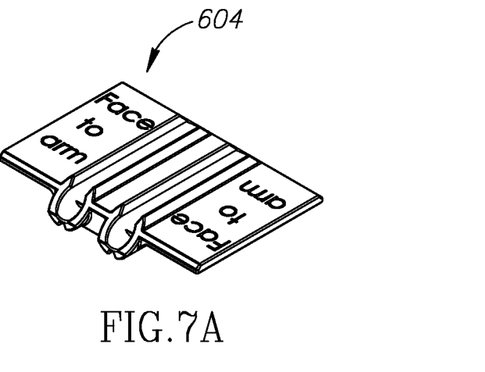
FIG. 7A illustrates a top perspective view of a tube holding member of the device in FIGS. 6A to 6F.
Figure 7B:
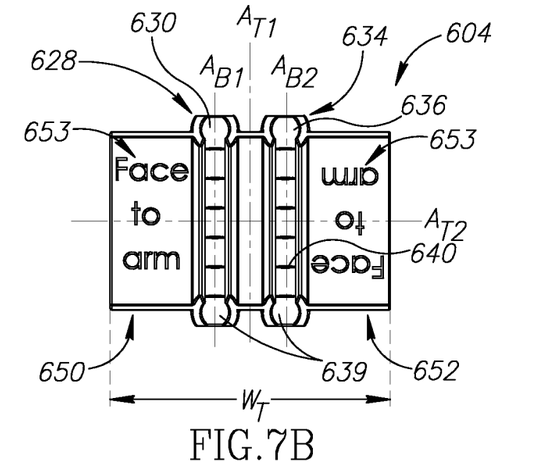
FIG. 7B illustrates a front view of the tube holding member in FIG. 7A.
Figure 7C:
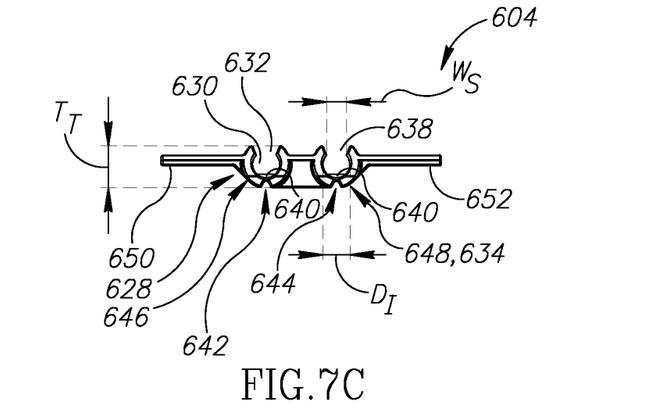
FIG. 7C illustrates a side view of the tube holding member in FIGS. 7A and 7B.
Figure 7D:
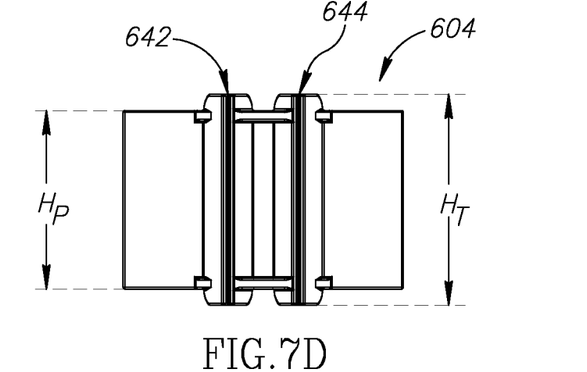
FIG. 7D illustrates a rear view, i.e. opposite to the front view shown in FIG. 7B, of the tube holding member in FIGS. 7A to 7C.

Referring to FIGS. 6D to 6F, the tourniquet 600 is shown in an unfolded state.

The elongate strip 602 can comprise opposite first and second surfaces 606, 608 connected by a peripheral edge 610.

The elongate strip 602 also comprises first and second ends 612, 614, and an intermediary portion 615 extending therebetween.

The peripheral edge 610 comprises: a first minor sub-edge 616 connecting the first and second surfaces 606, 608 at the first end 612; a second minor sub-edge 618 connecting the first and second surfaces 606, 608 at the second end 614; a first major sub-edge 620 connecting ends of the first and second minor sub-edges 616, 618; and a second major sub-edge 622 opposite the first major sub-edge 620 and connecting the first and second minor sub-edges 616, 618.

Stated differently, the elongate strip 602 can have a rectangular parallelepiped shape.

A longitudinal strip axis $A_D$ can extend through the first and second minor sub-edges 616, 618 and parallel with the first and second major sub-edges 620, 622.

While the elongate strip 602 is shown in an unstretched state, it will be understood that it may comprise of a stretchable material allowing it to be elongated along the longitudinal strip axis $A_D$.

The elongate strip 602 is flexible allowing it to be wrapped around a limb.

The tube holding member 604 may be attached to the first surface 606 at the first end 612.

As shown in FIG. 6F, a first fastening element 624 may be attached to the second surface 608 at the second end 614.

A second fastening element 626 may be attached to the second surface 608 at the first end 612. As shown, the second fastening element 626 can be located at a diametrically opposite side of the elongate strip 602 to the tube holding member 604.

The first and second fastening elements 624, 626 can be hook-and-loop fasteners, and at least the first surface 606 may be configured for detachable attachment to the fasteners 624, 626.

Referring now to FIGS. 7A to 7D the tube holding member 604 will be described in more detail.

The tube holding member 604 may comprise at least a first cylindrically shaped wall 628 defining a bore 630, and a slit aperture 632 extending along the cylindrically shaped wall 628.

The tube holding member 604 may also comprise a second cylindrically shaped wall 634 defining a bore 636, and a slit aperture 638 extending along the cylindrically shaped wall 634.

Each bore 630, 636 can have a longitudinal bore axis $A_{B1}$, $A_{B2}$.

Reverting briefly to FIG. 6F, the cylindrically shaped walls 628, 634 may notably protrude further than the elongate strip 602 in a direction transverse to the longitudinal axis $A_D$. Preferably, the cylindrically shaped walls 628, 634 can protrude further than the elongate strip 602 in two directions (e.g., extending past both the first and second major sub-edges 620, 622).

An inner surface 639 of each cylindrically shaped wall may be formed with one or more anti-slip ribs 640 oriented, for example, perpendicular to an associated longitudinal bore axis $A_{B1}$, $A_{B2}$.

Each cylindrically shaped wall 628, 634 may be formed with a groove 642, 644. The groove 642, 644 may be formed along an outer surface 646, 648 of the associated cylindrically shaped wall 628, 634.

The tube holding member 604 may also comprise planar shaped plates 650, 652, extending from opposite sides of the cylindrically shaped walls 628, 634.

The planar shaped plates 650, 652 can provide instructions 653, for example stating "Face to arm", for first aid providers as to correct application orientation of the tube holding member 604 on a limb (FIGS. 8A to 8D). It will be understood that under pressure of an emergency, even simple application procedures may be forgotten. As shown, the words can be oriented in opposite directions to further simplify use during an emergency.

A tube holding member height $H_T$ of each cylindrically shaped wall 628, 634 may be greater than a parallel plate height $H_P$ length of the planar shaped plates 650, 652.

It will be noted that a tube holding member thickness $T_T$ is significantly smaller than the other dimensions (tube holding member height $H_T$, tube holding member width $W_T$) allowing the tube holding member 604 to be viewed as having a planar shape.

The tube holding member 604 can be symmetric on either side of a first tube axis $A_{T1}$ which extends through the middle of the tube holding member 604 and parallel with the longitudinal bore axes $A_{B1}$, $A_{B2}$.

The tube holding member 604 can be symmetric on either side of a second tube axis $A_{T2}$ which extends through the middle of the tube holding member 604 and perpendicular with the longitudinal bore axes $A_{B1}$, $A_{B2}$.

In an axial view of the tube holding member 604 (FIG. 7C), the first and second plates 650, 652 may extend at a height about half-way between the slit aperture 632, 638 and a connection region 654 of the tube holding member 604 and the elongate strip 602. More precisely, in the example shown, the first and second plate members 650, 652 may extend at a height closer to the slit aperture 632, 638.

Each slit aperture 632, 638 of the tube holding member 604 may extend transverse or, preferably, perpendicular (as shown in FIG. 6D) to the longitudinal strip axis $A_D$.

Each slit aperture 632, 638 may have a width $W_S$ less than an inner diameter $D_I$ of each cylindrically shaped wall 628, 634.

Figure 8A:
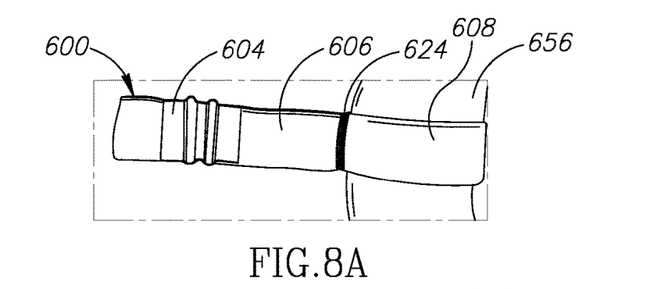
FIG. 8A illustrates the tourniquet in FIGS. 6A to 6F, in a first operational state, encircling and compressing a limb to provide a tourniquet function.

Referring now to FIG. 8A which illustrates the tourniquet 600 in FIGS. 6A to 6F, in a first operational state encircling and compressing a limb 656 to provide a tourniquet function.

More precisely, the first fastening element 624 has been fastened to the first surface 606 in a tight manner around the limb 656.

A catheter can then be applied to the limb (as shown in FIG. 2).

The tourniquet 600 is then removed from the limb 656 and refastened on the limb 656, specifically securing a catheter tube 657, and even more specifically securing tube portions 658, 660 of the same tube 657.

More specifically, since the cylindrically shaped wall 628, 634 protrude from the elongate strip 602 the tube holding member 604 can be positioned over the tube portions 658, 660 when a first-aid provider is facing the second surface 608 (the view shown in FIG. 6F). Since the cylindrically shaped wall 628, 634 protrude and are still partially visible in such view, the tourniquet 600 can be applied closer to a catheter with more ease than would otherwise be the case.

Figure 8B:
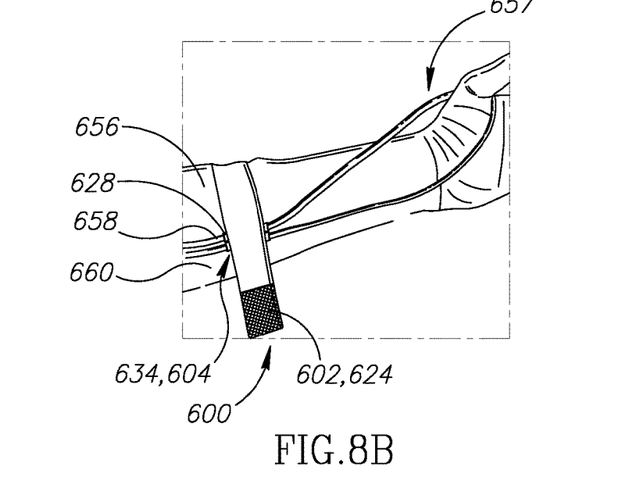
FIG. 8B illustrates a view of the tourniquet in FIG. 8A, in a second operational state, encircling a different portion of the same limb and securing two catheter tube portions (the remainder of the catheter assembly not being shown in FIGS. 8B to 8D) to provide a catheter securing function.
Figure 8C:
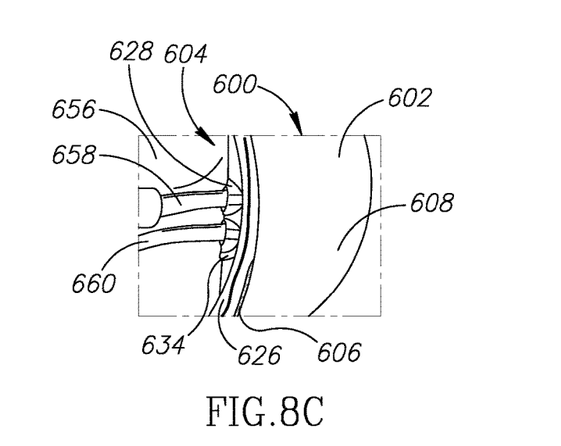
FIG. 8C illustrates an enlarged view of a portion of the tourniquet shown in the operational state in FIG. 8B.

In the position shown in FIGS. 8B and 8C, the tube portions 658, 660 have been inserted into the first and second bores 630, 636 via the slit apertures 632, 638 which flexed open during insertion (assisted by the grooves 642, 644) and then reverted to their original position. Friction from the anti-slip ribs 640 and a tight fit of the cylindrically shaped wall 628, 634 around the tube portions 658, 660 assist in securing the tube portions 658, 660 in position.

Additionally, after the tube portions 658, 660 are secured, the second fastening element 626 is fastened by wrapping the elongate strip 602 around the limb 656 such that it is fastened to the first surface 606 in a tight manner (FIG. 8C).

Figure 8D:
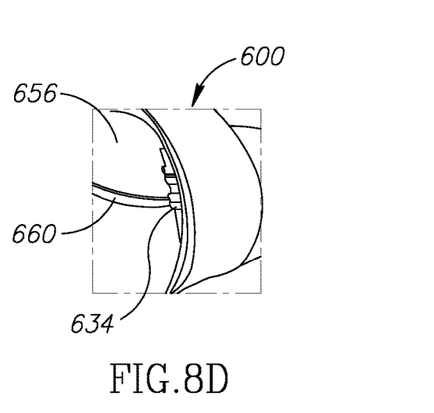
FIG. 8D illustrates a similar view to the view in FIG. 8C, except with the tourniquet in an alternative operational state in which it secures only a single catheter tube.

FIG. 8D demonstrates that a single tube portion 658 can be secured by the same tourniquet 600. It will also be understood that a tube holding member (not shown) with a single cylindrically shaped wall would also suffice for such application.

It will be understood that the embodiments exemplified above are not intended to preclude non-exemplified embodiments from the scope of the claims.

What is claimed is:

1. A tourniquet comprising:
   a flexible elongate strip and
   a tube holding member;
   the elongate strip comprising:
     opposite first and second surfaces connected by a peripheral edge;
     first and second ends;
     at least one fastening element attached to the elongate strip; and
     the first and/or second surface being configured for detachable attachment to the at least one fastening element;
   the tube holding member being non-detachably attached to the elongate strip and comprising:
     at least one cylindrically shaped wall defining a bore, and a slit aperture extending along the at least one cylindrically shaped wall;

wherein:

the at least one fastening element comprises a first fastening element non-detachably attached to the first end of the elongate strip and a second fastening element non-detachably attached to the second end of the elongate strip; and wherein:

the tube holding member is a rigid component having a planar shape.

2. The tourniquet according to claim 1, wherein the elongate strip is stretchable.

3. The tourniquet according to claim 1, wherein the first and second fastening elements are both non-detachably attached to the second surface of the elongate strip.

4. The tourniquet according to claim 3, wherein the tube holding member is attached to the first surface of the elongate strip.

5. The tourniquet according to claim 4, wherein the second fastening element is located at a diametrically opposite side of the elongate strip to the tube holding member.

6. The tourniquet according to claim 1, wherein each of the first and second fastening elements, is a hook-and-loop fastener.

7. The tourniquet according to claim 1, wherein the slit aperture is positioned to be at a diametrically opposite side of the at least one cylindrically shaped wall from the elongate strip.

8. The tourniquet according to claim 1, wherein the slit aperture extends perpendicular to a longitudinal axis of the elongate strip.

9. The tourniquet according to claim 1, wherein the slit aperture has a width less than an inner diameter of the at least one cylindrically shaped wall.

10. The tourniquet according to claim 1, wherein the tube holder member further comprises first and second planar shaped plates extending on opposite sides of the at least one cylindrically shaped wall.

11. The tourniquet according to claim 1, wherein the at least one cylindrically shaped wall protrudes further than the elongate strip in a direction transverse to a longitudinal axis of the elongate strip.

12. The tourniquet according to claim 1, wherein an inner surface of each of the at least one cylindrically shaped wall is formed with one or more anti-slip ribs oriented transverse or perpendicular to a longitudinal bore axis of the at least one cylindrically shaped wall.

13. The tourniquet according to claim 1, wherein each of the at least one cylindrically shaped wall is formed with a groove.

14. The tourniquet according to claim 13, wherein each groove is formed along an outer surface of the at least one cylindrically shaped wall.

15. The tourniquet according to claim 13 wherein each groove is located at a diametrically opposite portion of the at least one cylindrically shaped wall from the slit aperture thereof.

16. The tourniquet according to claim 13, wherein each groove extends parallel with the slit aperture of the at least one cylindrically shaped wall.

17. The tourniquet according to claim 1, wherein the tourniquet is devoid of electronic, hydraulic and pneumatic components or components configured to connect to electronic, hydraulic or pneumatic components.

18. The tourniquet according to claim 1, wherein the tourniquet comprises no more than four functional components.

19. A tourniquet comprising:

a flexible elongate strip and a tube holding member;

the elongate strip comprising:

opposite first and second surfaces connected by a peripheral edge;

first and second ends;

at least one fastening element non-detachably attached to the elongate strip;

and the first and/or second surface being configured for detachable attachment to the at least one fastening element;

the tube holding member being non-detachably attached to the elongate strip and comprising:

at least one cylindrically shaped wall defining a bore, and a slit aperture extending along the at least one cylindrically shaped wall;

wherein:

the at least one fastening element comprises a first fastening element located at, and non-detachably attached to, a diametrically opposite side of the elongate strip to the tube holding member; and wherein:

the tube holding member is a rigid component having a planar shape.

20. A method of applying a tourniquet, the tourniquet comprising:

a flexible elongate strip and a tube holding member being a rigid component having a planar shape;

the elongate strip comprising:

opposite first and second surfaces connected by a peripheral edge;

first and second ends;

at least one fastening element non-detachably attached to the elongate strip; and the first and/or second surface being configured for detachable attachment to the at least one fastening element;

the tube holding member being non-detachably attached to the first surface of the elongate strip and comprising:

at least one cylindrically shaped wall defining a bore, and a slit aperture extending along the at least one cylindrically shaped wall;

wherein the at least one fastening element comprises a fastening element located at a diametrically opposite side of the elongate strip to the tube holding member;

the method of applying comprising:

connecting the tube holding member to a tube of a catheter with the slit aperture facing a limb; and wrapping the elongate strip around the limb and fastening the fastening element, which is located at, and non-detachably attached to, a diametrically opposite side of the elongate strip to the tube holding member, in such manner that part of the strip covers the tube holding member.

* * * * *